(12) United States Patent  
Govari

(10) Patent No.: US 11,766,206 B2
(45) Date of Patent: Sep. 26, 2023

(54) ELECTRODE ARRANGEMENT TO SENSE CARDIAC WAVE VECTOR

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 1005 days.

(21) Appl. No.: 16/228,403

(22) Filed: Dec. 20, 2018

(65) Prior Publication Data

US 2020/0196895 A1 Jun. 25, 2020

(51) Int. Cl.

| | |
|---|---|
| *A61B 18/18* | (2006.01) |
| *A61B 5/00* | (2006.01) |
| *A61B 5/287* | (2021.01) |
| *A61B 5/341* | (2021.01) |
| *A61B 5/352* | (2021.01) |

(52) U.S. Cl.
CPC .............. *A61B 5/287* (2021.01); *A61B 5/341* (2021.01); *A61B 5/352* (2021.01); *A61B 5/6852* (2013.01); *A61B 2562/0209* (2013.01); *A61B 2562/125* (2013.01)

(58) Field of Classification Search
CPC ......... A61B 5/349; A61B 5/287; A61B 5/316; A61B 5/341; A61B 5/318; A61B 5/339; A61B 5/0538; A61B 34/20; A61B 5/363; A61B 5/053; A61B 5/283; A61B 2018/00839; A61B 5/0245; A61B 5/0006; A61B 2017/00053; A61B 5/02125; A61B 5/066; A61B 5/063; A61B 5/361; A61B 2017/00026

USPC ........ 600/372–374, 381, 466–467, 508–509, 600/512–513, 515–523
See application file for complete search history.

(56) References Cited

U.S. PATENT DOCUMENTS

| | | |
|---|---|---|
| 4,630,611 A | 12/1986 | King |
| 5,127,403 A | 7/1992 | Brownlee |
| 5,450,846 A * | 9/1995 | Goldreyer .............. A61B 5/339 600/374 |
| 5,803,084 A * | 9/1998 | Olson .................... A61B 5/339 600/512 |

(Continued)

OTHER PUBLICATIONS

Anter et al. "Activation Mapping With Integration of Vector and Velocity Information Improves the Ability to Identify the Mechanism and Location of Complex Scar-Related Atrial Tachycardias" Circulation: Arrhythmia and Electrophysiology. Jul. 2018. (Year: 2018).*

(Continued)

*Primary Examiner* — Joseph A Stoklosa
*Assistant Examiner* — Brian M Antiskay
(74) *Attorney, Agent, or Firm* — Dergosits & Noah LLP; Todd A. Noah

(57) ABSTRACT

A system includes two or more pairs of electrodes and a processor. The electrodes are disposed over a distal end of a catheter for insertion into a heart of a patient. The electrodes in each pair are parallel with one another, and the pairs are not parallel with one another. The processor is configured to receive electrophysiological (EP) signals acquired by the pairs of electrodes, and, based on a timing of the received EP signals, calculate a local direction at which the received EP signals propagate in the heart.

12 Claims, 3 Drawing Sheets

(56) References Cited

U.S. PATENT DOCUMENTS

| | | | |
|---|---|---|---|
| 6,236,883 B1* | 5/2001 | Ciaccio | A61B 5/363 |
| | | | 600/515 |
| 6,799,064 B1 | 9/2004 | Hassett | |
| 8,456,182 B2 | 6/2013 | Bar-Tal et al. | |
| 2002/0055674 A1* | 5/2002 | Ben-Haim | A61B 5/6859 |
| | | | 600/374 |
| 2005/0209525 A1* | 9/2005 | Bojovic | A61B 5/341 |
| | | | 600/512 |
| 2009/0204193 A1 | 8/2009 | Kokones et al. | |
| 2010/0268059 A1* | 10/2010 | Ryu | A61B 5/283 |
| | | | 600/407 |
| 2013/0317334 A1 | 11/2013 | Bar-Tal et al. | |
| 2014/0343388 A1* | 11/2014 | Thakur | A61B 5/7221 |
| | | | 600/374 |
| 2015/0208942 A1* | 7/2015 | Bar-Tal | A61B 5/361 |
| | | | 600/509 |
| 2016/0045133 A1* | 2/2016 | Balachandran | A61B 5/287 |
| | | | 600/509 |
| 2016/0184008 A1* | 6/2016 | Papaioannou | A61B 5/6852 |
| | | | 606/41 |
| 2017/0079542 A1 | 3/2017 | Spector | |
| 2017/0202472 A1* | 7/2017 | Zeidan | A61B 5/6856 |
| 2017/0281193 A1* | 10/2017 | Asirvatham | A61B 17/12177 |

OTHER PUBLICATIONS

European Search Report for corresponding EPA No. 19217979.4 dated Apr. 29, 2020.

Schoenwald et al., "A Method for Determining Local Activation Direction in the Atrium", Engineering in Medicine and Biology Society, pp. 1-2, 1994.

Coldreyer, B.N. et al., "A New Orthogonal Lead for P Synchronous Pacing", Pace-Pacing and Clinical Electrophysiology, vol. 4, pp. 638-644, Nov. 1, 1981.

* cited by examiner

ELECTRODE ARRANGEMENT TO SENSE CARDIAC WAVE VECTOR

FIELD OF THE INVENTION

The present invention relates generally to electro-anatomical mapping, and particularly to cardiac electro-anatomical mapping.

BACKGROUND OF THE INVENTION

Invasive diagnostic cardiology techniques for generating a cardiac electro-anatomical map have been previously described in the patent literature. For example, U.S. Patent Application Publication 2017/0079542 describes catheters, systems, and related methods for optimized mapping, minimizing, and treating of cardiac fibrillation in a patient, including an array of at least one stacked electrode pair. In some embodiments, each electrode pair includes a first electrode and a second electrode, wherein each electrode pair is configured to be orthogonal to a surface of a cardiac tissue substrate. In some embodiments, each first electrode is in contact with the surface to record a first signal, and each second electrode is separated from the first electrode by a distance which enables the second electrode to record a second signal. The catheter is configured to obtain one or more measurements from at least the first signal and the second signal in response to electrical activity in the cardiac tissue substrate indicative of a number of electrical circuit cores and distribution of the electrical circuit cores for a duration across the cardiac tissue substrate.

As another example, U.S. Patent Application Publication 2002/0055674 describes an elongate probe apparatus for insertion into the body of a subject, comprising: a structure having a substantially rigid configuration. A plurality of physiological sensors on the probe generate signals responsive to a physiological activity, wherein the sensors having substantially fixed positions on the structure in said configuration. One or more devices generate position signals indicative of the positions of the physiological sensors on the structure in said configuration. Bipolar signals can be decomposed into components parallel and perpendicular to an axis passing through any a pair of electrodes, and the amplitude of the bipolar signal between these electrodes will be proportional to the relative magnitude of the parallel component.

SUMMARY OF THE INVENTION

An embodiment of the present invention provides a system including two or more pairs of electrodes and a processor. The electrodes are disposed over a distal end of a catheter for insertion into a heart of a patient. The electrodes in each pair are parallel with one another, and the pairs are not parallel with one another. The processor is configured to receive electrophysiological (EP) signals acquired by the pairs of electrodes, and, based on a timing of the received EP signals, calculate a local direction at which the received EP signals propagate in the heart.

In some embodiments, the pairs of strip electrodes are orthogonal with one another.

In an embodiment, the electrodes include linear strips. In another embodiment, the electrodes have an oval shape.

In some embodiments, the processor is configured to identify that the local direction is normal to a surface of the heart, by detecting that a timing of arrival of the EP signals to at least two pairs of electrodes is equal up to a given tolerance.

In some embodiments, the processor is further configured to calculate a magnitude of the received EP signals.

There is additionally provided, in accordance with an embodiment of the present invention, a method including receiving electrophysiological (EP) signals acquired by two or more pairs of electrodes disposed over a distal end of a catheter for insertion into a heart of a patient, wherein (i) the electrodes in each pair are parallel with one another, and (ii) the pairs are not parallel with one another. Based on a timing of the received EP signals, a direction at which the received EP signals propagate in the heart is calculated.

In some embodiments, calculating the local direction includes identifying that the local direction is normal to a surface of the heart, by detecting that a timing of arrival of the EP signals to at least two pairs of electrodes is equal up to a given tolerance.

In some embodiments, the method further includes calculating a magnitude of the received EP signals.

There is further provided, in accordance with an embodiment of the present invention, a manufacturing method, including disposing over a distal end of a catheter for insertion into a heart of a patient two or more pairs of electrodes, wherein (i) the electrodes in each pair are parallel with one another, and (ii) the pairs are not parallel with one another. The two or more pairs of electrodes are electrically connected to a connector located in a proximal end of the catheter.

The present invention will be more fully understood from the following detailed description of the embodiments thereof, taken together with the drawings in which:

DETAILED DESCRIPTION OF EMBODIMENTS

Overview

Figure 1:
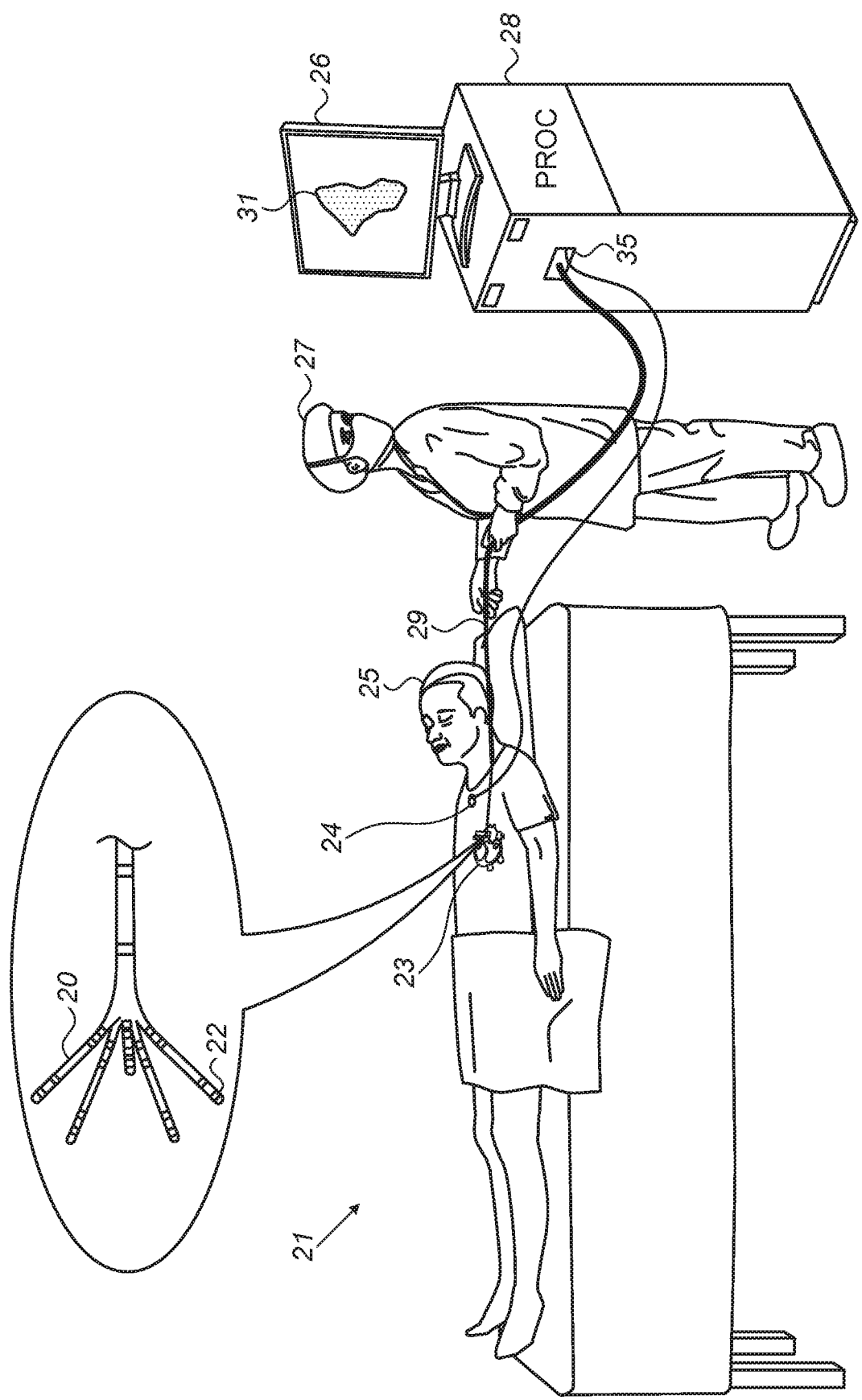
FIG. 1 is a schematic, pictorial illustration of a system for electro-anatomical mapping, in accordance with an embodiment of the present invention.

Intracardiac electrophysiological (EP) mapping (also named hereinafter "electro-anatomical mapping") is a catheter-based method that is sometimes applied to characterize cardiac EP abnormalities, such as an arrhythmia. In a typical catheter-based procedure, a distal end of a catheter, which comprises sensing-electrodes, is inserted into the heart to sense EP signals. In order to create an EP map, the physician moves the distal end inside the heart, and an EP mapping system acquires EP signals at various cardiac locations, as well as acquiring the respective locations.

However, for diagnostics, the propagation direction of the EP wave may also be needed. Finding such a direction over cardiac tissue conventionally requires the system to perform laborious calculations. For example, the direction of propagation of the cardiac wave can be found by creating a local activation time (LAT) map of sections of the heart. In addition to being relatively time-consuming, such a spatial analysis of timing diagrams (e.g., an LAT map) cannot be performed easily and quickly, since, for example, it must first collect data points from multiple cardiac locations.

Embodiments of the present invention that are described hereinafter provides electrode-pair patterns disposed on a substrate over the distal end of a catheter. When brought into physical contact with the inner surface of the heart, the electrode-pair patterns are configured to acquire electrical signals indicative of a direction of a travelling EP wave. In some embodiments, the distal end of the catheter comprises two or more pairs of electrodes, wherein (i) the electrodes in each pair are parallel with one another, and (ii) the pairs are not parallel with one another. A processor is configured to receive EP signals acquired by the pairs of electrodes, and, based on a timing of the received EP signals, calculate a local direction at which the received EP signals propagate in the heart.

In some embodiments, an electrode-pair pattern is configured to measure bi-polar EP signals. In such embodiments, each electrode pair comprises parallel strip electrodes, where one electrode pair is aligned orthogonally to the other pair, as further described below.

In some embodiments, as an EP wave travels through a cardiac location, each of the two or more electrode pairs of the electrode-pair pattern acquire the EP potential at a different timing, and the processor analyzes the relative timing between electrodes of the arrival of potential (e.g., by comparing times where the peak potential occurs), and analyzes the signal strength so as to provide a direction and a magnitude the traveling EP wave, respectively.

In an embodiment, the processor additionally indicates whether, at a certain location, the travelling EP wave is propagating in a normal direction relative to the heart surface (i.e., normal to a direction along a plane of the substrate). The processor identifies such an EP wave when the timing of signal arrival, measured by two or more pairs of electrodes of an electrode-pair pattern, is substantially equal (i.e., equal up to a given tolerance), as described below. Such a normal travelling wave may occur in certain parts of the heart. For example, such normal direction propagation may occur at a vicinity of sharp termination of healthy tissue near scar tissue.

Typically, the processor is programmed in software containing a particular algorithm that enables the processor to conduct each of the processor related steps and functions outlined above.

The disclosed electrode-pair patterns enable a processor to readily estimate, in real time, a local direction along which an EP wave propagates, including detecting an EP wave propagating in a normal direction. In this way the disclosed technique may improve the diagnostic value of an intracardiac EP mapping procedure.

System Description

FIG. 1 is a schematic, pictorial illustration of a system 20 for electro-anatomical mapping, in accordance with an embodiment of the present invention. FIG. 1 depicts a physician 27 using an electro-anatomical catheter 29 to perform an electro-anatomical mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject signals from and/or to the tissue of heart 23. A processor 28 receives these signals via an electrical interface 35, and uses information contained in these signals to construct an electro-anatomical map 31. During and/or following the procedure, processor 28 may display electro-anatomical map 31 on a display 26.

During the procedure, a tracking system is used to track the respective locations of sensing-electrodes 22, such that each of the signals may be associated with the location at which the signal was acquired. For example, the Active Current Location (ACL) system, made by Biosense-Webster (Irvine, Calif.), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface-electrodes 24, that are coupled to the skin of patient 25. For example, three surface-electrodes 24 may be coupled to the patient's chest, and another three surface-electrodes may be coupled to the patient's back. (For ease of illustration, only one surface-electrode is shown in FIG. 1.) Electric currents are passed between electrodes 22 inside heart 23 of the patient, and surface-electrodes 24. Processor 28 calculates an estimated location of all electrodes 22 within the patient's heart based on the ratios between the resulting current amplitudes measured at surface-electrodes 24 (or between the impedances implied by these amplitudes) and the known positions of electrodes 24 on the patient's body. The processor may thus associate any given impedance signal received from electrodes 22 with the location at which the signal was acquired.

Processor 28 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm that enables processor 28 to perform the disclosed steps, as described below.

The example illustration shown in FIG. 1 is chosen purely for the sake of conceptual clarity. Other types of sensing catheters, such as the Lasso® Catheter (produced by Biosense-Webster) may equivalently be employed. Contact sensors may be fitted at the distal end of electro-anatomical catheter 29. As noted above, other types of electrodes, such as those used for ablation, may be utilized in a similar way, fitted to electrodes 22 for acquiring the needed position data. Thus, an ablation electrode used for collecting position data is regarded, in this case, as a sensing-electrode. In an optional embodiment, processor 28 is further configured to indicate the quality of physical contact between each of the electrodes 22 and an inner surface of the cardiac chamber during measurement.

The elements of system 21 and the methods described herein may be performed by applying voltage gradients between ACL patch electrodes 49 or other skin-attached electrodes, and measure induced intrabody potentials with sensing electrodes 22 on catheter 29 (e.g., using the Carto® 4 technology produced by Biosense-Webster). Thus, embodiments of the present invention apply to any position sensing method used for EP mapping in which a sensing-electrode generates signals indicative of its position in the heart.

Electrode Arrangement to Sense Cardiac Wave Vector

Figure 2A:
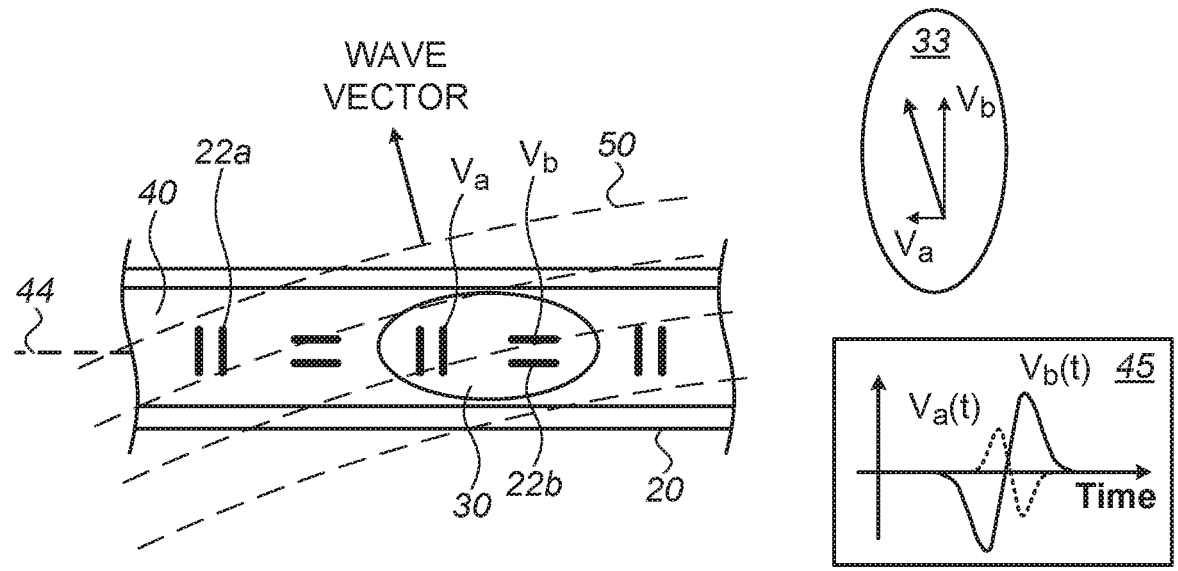
FIGS. 2A and 2B are schematic, pictorial illustrations of electrode-pair patterns configured to acquire electrical signals indicative of a direction of an electrophysiological (EP) wave, in accordance with embodiments of the present invention.
Figure 2B:
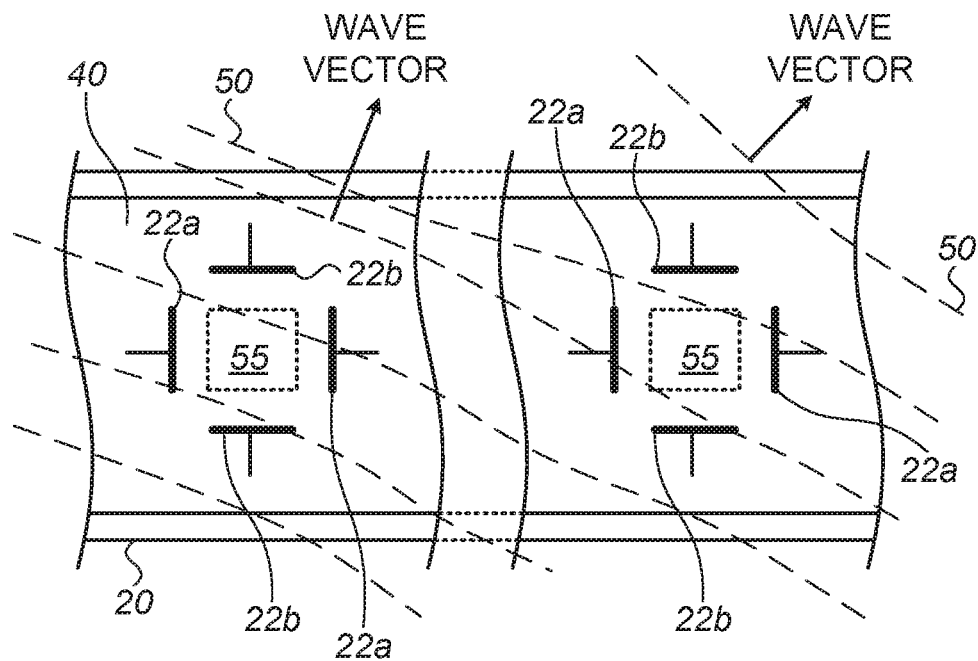

FIGS. 2A and 2B are schematic, pictorial illustrations of electrode-pair patterns 30A and 30B, respectively, configured to acquire electrical signals indicative of a direction of an electrophysiological (EP) wave 50, in accordance with embodiments of the present invention.

Relative timings of wave arrival (e.g., differences between times at which a maximal potential value is sensed by each electrode) are derived by a processor, based on the acquired waveforms. The electrodes measure the electrical potential of travelling EP wave 50 relative to a common electrode, such as a surface body electrode, or an electrode of a coronary sinus catheter that is placed inside the coronary sinus, or using one of the electrodes as a common electrode.

FIG. 2A shows an embodiment at which electrode-pair pattern 30a (shown as orthogonal electrode pairs 22a1 and 22a2) is aligned about a common center. As seen, an area 55 is delimited by electrode pairs 22a1 and 22a2. Area 55 is finite (i.e., electrodes are not aligned over a line), so that the electrode-pair pattern encodes in one to one agreement (i.e., "spans") all possible in-plane directions of propagation of EP wave 50.

In an embodiment, arm 20 is disposed with a preset number of such electrode-pair patterns, two of which are seen in FIG. 2A.

To show how electrode-pair pattern 30A encodes, in a one-to-one agreement, a direction of propagation of a travelling EP wave in the plane of substrate 40, the four electrodes are marked in the inset of FIG. 2A as E1, E2, E3, and E4. A resulting encoding of the timing of arrival of EP potential of the travelling wave shown, in the inset, is (1)-(4)-(3)-(2), i.e., (1432), which is a timed order at which respective electrodes E1-E2-E3-E4 sense the wave.

In the inset of FIG. 2A the electrodes are shown as circular objects, although the shape of the electrodes may vary, being, for example, oval.

In case of similar propagation directions, the order of encoded timing described above usually remains the same, but the quantitative differences in timings between electrodes always changes. Using the acquired quantitative timing differences, processor 28 determines a unique local direction of propagation, for example, relative to a longitudinal axis 44 of a catheter arm 20. Thus, as demonstrated in the inset of FIG. 2A, the local direction at which the EP wave propagates (i.e., the local wave vector of the EP wave) can be extracted by measuring the relative timings.

In an embodiment, in order to measure different timings of a travelling wave for electrodes that are typically spaced up to several millimeters apart, EP mapping system 21 acquires the time-dependent signals at a rate of tens of MHz.

As another example, FIG. 2B shows an embodiment in which electrode-pair pattern 30b comprises electrode pair 22b1 that is aligned orthogonally to a neighboring pair 22b2. Pattern 30 repeats itself so that a preset number of patterns 30 is disposed on a substrate 40 attached to arm 20 of the catheter. This arrangement is further illustrated in the inset of FIG. 2B using circular electrodes.

Figure 3:
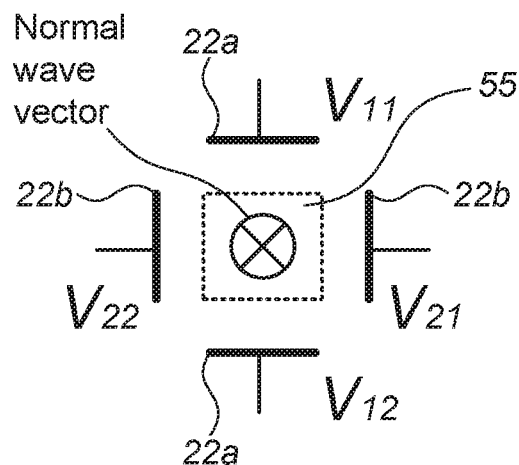
FIG. 3 is a schematic, pictorial illustration of a travelling EP wave propagating in a normal direction and detected by the electrode-pair pattern of FIG. 2A, in accordance with embodiments of the present invention.

In some embodiments, electrode-pair patterns 30A and 30B are configured to detect an EP wave propagating in a normal direction, as described in FIG. 3 for the electrode-pair pattern embodiment shown in FIG. 2A.

The electrode configurations described in FIG. 2 are brought by way of example. Other configurations, such as those aligned in various angles relative to a longitudinal axis of arms 20, are possible. The disclosed substrate may be made of flexible materials, allowing the wrapping of the electrode-pair patterns over arms 20 in various angles, for example, to ensure measuring a sufficiently strong EP signal at any catheter orientation relative to tissue. In an embodiment, arm 20 is disposed with both patterns 30a and 30b.

FIG. 3 is a schematic, pictorial illustration of a travelling EP wave propagating in a normal direction 57 and detected by the electrode-pair pattern 30A of FIG. 2A, in accordance with embodiments of the present invention.

FIG. 3 shows a unique case of EP propagation that results in all four time-dependent potentials $V_1$, $V_2$, $V_3$, and $V_4$ being practically the same, at a relevant time window, when such finite signals exist. An EP wave causing the above must have the local wave vector of the EP wave aligned normally to substrate 40, as indicated by direction into substrate 40 at area 55. Thus, the disclosed electrode-pair pattern is capable of detecting propagation in tissue that is largely normal to an "in-plane" propagation. As noted above, such propagation may occur in the vicinity of sharp termination of healthy tissue, for example near scar tissue.

In an embodiment, processor 28 determines a direction of the largely normal propagation (e.g., out of a substrate or into a substrate) based on the small, but measurable, in-plane component of the largely normally-directed wave vector.

Figure 4:
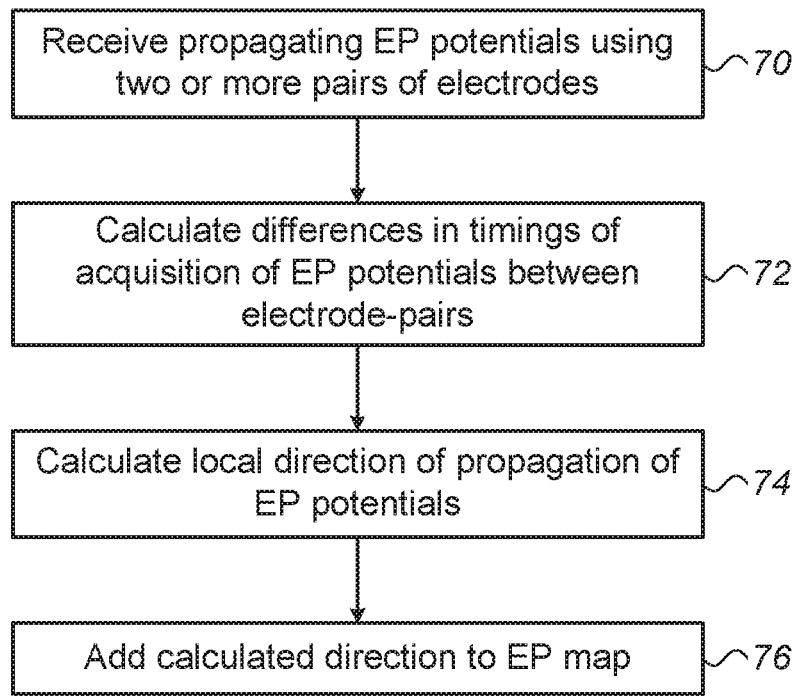
FIG. 4 is a flow chart that schematically illustrates a method and algorithm for detecting a direction of a travelling EP wave, in accordance with an embodiment of the present invention.

FIG. 4 is a flow chart that schematically illustrates a method and algorithm for detecting a direction of a travelling EP wave, in accordance with an embodiment of the present invention. The process begins with physician 30 acquiring propagating cardiac EP potentials using two or more pairs of electrodes comprised in electrode-pair patterns, such as patterns 30a and/or 30b, fitted at a distal end of a catheter inside heart 26, at EP signals acquisition step 70. Next, using on the acquired EP signals and using the algorithm according to the presented embodiment carried out by the processer, processor 28 calculates differences in timings of acquisition of the acquired EP signals (i.e., potentials) between electrode-pairs, at an EP wave timings calculation step 72.

Next, processor 28 calculates a local direction of propagation of the EP wave (i.e., a wave vector), at a direction calculation step 74. Processor 28 adds the calculated direction (or indicated, in case the direction is normal) to an EP map, at an EP map updating step 76.

The example flow chart shown in FIG. 4 is chosen purely for the sake of conceptual clarity. In alternative embodiments, additional steps may be used, such as detection of a degree of physical contact of any of the electrodes with tissue.

Although the embodiments described herein mainly address cardiac EP mapping, the methods and systems described herein can also be used in other applications, such as in neurology.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:

two or more electrode pairs disposed over a distal end of a catheter for insertion into a heart of a patient, the two or more electrode pairs being positioned in a same semicylindrical portion of the catheter along a longitudinal axis of the catheter and configured in a predetermined pattern to acquire electrical signals indicative of a direction of a propagating electrophysiological (EP) wave relative to the longitudinal axis of the catheter, wherein the predetermined pattern is configured such that: (i) the electrodes in each pair are parallel with one another, (ii) the electrodes in each electrode pair extend substantially in a same plane and not parallel to the electrodes in a neighboring electrode pair, and (iii) each electrode pair is aligned about a common center with the neighboring electrode pair in the same semicylindrical portion; and a processor, which is configured to:

receive EP signals acquired by the pairs of electrodes;

calculate a difference in timing of acquisition of the EP signal received by each electrode pair of the electrode pairs, respectively;

calculate a local direction at which the received EP signals propagate in the heart in the same plane of the catheter, in response to the calculated difference in timing of acquisition of the received EP signals by each electrode pair of electrode pairs; and add the calculated local direction to an EP map.

2. The system according to claim 1, wherein the pairs of electrodes are orthogonal with one another.

3. The system according to claim 1, wherein the electrodes comprise linear strips.

4. The system according to claim 1, wherein the electrodes have an oval shape.

5. The system according to claim 1, wherein the processor is configured to identify that the local direction is normal to a surface of the heart, by detecting that a timing of arrival of the EP signals to at least two pairs of electrodes is equal up to a given tolerance.

6. The system according to claim 1, wherein the processor is further configured to calculate a magnitude of the received EP signals.

7. A method, comprising:

receiving electrophysiological (EP) signals acquired by two or more electrode pairs disposed over a distal end of a catheter for insertion into a heart of a patient, the two or more electrode pairs positioned in a same semicylindrical portion of the catheter along a longitudinal axis of the catheter and configured in a predetermined pattern to acquire electrical signals indicative of a direction of a propagating EP wave relative to the longitudinal axis of the catheter, wherein the predetermined pattern is configured such that (i) the electrodes in each pair are parallel with one another, (ii) the electrodes in each electrode pair extend substantially in a same plane and not parallel to the electrodes in a neighboring electrode pair, and (iii) each electrode pair is aligned about a common center with the neighboring electrode pair in the same semicylindrical portion;

calculating a difference in timing of acquisition of the EP signal received by each electrode pair of the electrode pairs, respectively;

calculating a local direction at which the received EP signals propagate in the heart in the same plane of the catheter, in response to the calculated difference in timing of acquisition of the received EP signals by each electrode pair of electrode pairs; and adding the calculated local direction to an EP map.

8. The method according to claim 7, wherein calculating the local direction comprises identifying that the local direction is normal to a surface of the heart, by detecting that a timing of arrival of the EP signals to at least two pairs of electrodes is equal up to a given tolerance.

9. The method according to claim 7, and comprising calculating a magnitude of the received EP signals.

10. A computer program product, comprising a non-transitory computer-readable medium having computer-readable program code embodied therein to be executed by one or more processors, the program code including instructions to:

receive electrophysiological (EP) signals acquired by two or more electrode pairs disposed over a distal end of a catheter for insertion into a heart of a patient, the two or more electrode pairs positioned in a same semicylindrical portion of the catheter along a longitudinal axis of the catheter and configured in a predetermined pattern to acquire electrical signals indicative of a direction of a propagating EP wave relative to the longitudinal axis of the catheter, wherein the predetermined pattern is configured such that: (i) the electrodes in each pair are parallel with one another, (ii) the electrodes in each electrode pair extend substantially in a same plane and not parallel to the electrodes in a neighboring electrode pair, and (iii) each electrode pair is aligned about a common center with the neighboring electrode pair in the same semicylindrical portion;

calculate a difference in timing of acquisition of the EP signal received by each electrode pair of the electrode pairs, respectively;

calculating a local direction at which the received EP signals propagate in the heart in the same plane of the catheter, in response to the calculated difference in timing of acquisition of the received EP signals by each electrode pair of electrode pairs;

and adding the calculated local direction to an EP map.

11. The computer program product according to claim 10, wherein calculating the local direction comprises identifying that the local direction is normal to a surface of the heart, by detecting that a timing of arrival of the EP signals to at least two pairs of electrodes is equal up to a given tolerance.

12. The computer program product according to claim 10, and comprising calculating a magnitude of the received EP signals.

* * * * *